US009986917B2

(12) United States Patent
Haverkost et al.

(10) Patent No.: US 9,986,917 B2
(45) Date of Patent: Jun. 5, 2018

(54) ENDOLUMINAL OSTIUM SENSOR ARRAY DEVICE

(71) Applicant: BOSTON SCIENTIFIC SCIMED, INC., Maple Grove, MN (US)

(72) Inventors: Patrick A. Haverkost, Brooklyn Center, MN (US); Adam D. Grovender, Brooklyn Park, MN (US); James M. Anderson, Corcoran, MN (US); Joel N. Groff, Delano, MN (US); Martin R. Willard, Burnsville, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 268 days.

(21) Appl. No.: 14/622,478

(22) Filed: Feb. 13, 2015

(65) Prior Publication Data

US 2015/0223704 A1    Aug. 13, 2015

Related U.S. Application Data

(60) Provisional application No. 61/939,617, filed on Feb. 13, 2014.

(51) Int. Cl.
| | |
|---|---|
| *A61B 5/00* | (2006.01) |
| *A61F 2/95* | (2013.01) |
| *A61B 5/02* | (2006.01) |
| *A61B 5/053* | (2006.01) |
| *A61F 2/958* | (2013.01) |

(Continued)

(52) U.S. Cl.
CPC ........ *A61B 5/02007* (2013.01); *A61B 5/0538* (2013.01); *A61B 5/6846* (2013.01);
(Continued)

(58) Field of Classification Search
CPC ............... A61B 5/6846; A61B 5/0538; A61B 2562/0257; A61B 2090/065; A61B 5/68586; A61B 5/02007; A61B 5/1076; A61B 5/1077; A61B 3/1005; A61F 2/958; A61F 2/915; A61F 2002/91575;
(Continued)

(56) References Cited

U.S. PATENT DOCUMENTS

| 5,238,004 A | 8/1993 | Sahatjian et al. |
| 6,270,493 B1 | 8/2001 | Lalonde et al. |

(Continued)

FOREIGN PATENT DOCUMENTS

| WO | 2008002654 A2 | 1/2008 |
| WO | 2012/058461 A1 | 5/2012 |

(Continued)

*Primary Examiner* — Christopher L Templeton
*Assistant Examiner* — George J Ulsh
(74) *Attorney, Agent, or Firm* — Seager, Tufte & Wickhem, LLP

(57) ABSTRACT

A sensor device for sensing endoluminal geometry may include an expandable element disposed on the distal region of a shaft. The expandable element may be configured to move a collapsed configuration and an expanded configuration. The expandable element may include one or more sensor elements configured to sense proximity of the sensor element to tissue. The sensor device may include an indicator configured to distinguish between contact of the sensor element with tissue, loss of contact and proximity of the sensor element to tissue.

19 Claims, 12 Drawing Sheets

(51) Int. Cl.
- *A61M 25/10* (2013.01)
- *A61F 2/915* (2013.01)
- *A61M 27/00* (2006.01)
- *A61B 90/00* (2016.01)

(52) U.S. Cl.
CPC ............ *A61B 5/6856* (2013.01); *A61F 2/958* (2013.01); *A61B 2090/065* (2016.02); *A61B 2562/0257* (2013.01); *A61F 2/915* (2013.01); *A61F 2/95* (2013.01); *A61F 2002/91575* (2013.01); *A61F 2250/0096* (2013.01); *A61M 25/104* (2013.01); *A61M 2027/004* (2013.01)

(58) Field of Classification Search
CPC .......... A61F 2250/0096; A61F 2/2496; A61M 25/104; A61M 2027/004
USPC ....................................................... 623/1.11
See application file for complete search history.

(56) References Cited

U.S. PATENT DOCUMENTS

| | | | |
|---|---|---|---|
| 6,508,803 | B1 | 1/2003 | Horikawa et al. |
| 7,651,520 | B2 | 1/2010 | Fischell et al. |
| 2007/0239252 | A1 | 10/2007 | Hopkins et al. |
| 2009/0105799 | A1 | 4/2009 | Hekmat et al. |
| 2010/0198040 | A1* | 8/2010 | Friedman ............. A61B 5/6885 600/374 |
| 2011/0071490 | A1 | 3/2011 | Kassab et al. |
| 2013/0150693 | A1* | 6/2013 | D'Angelo ............. A61B 5/036 600/373 |

FOREIGN PATENT DOCUMENTS

| | | |
|---|---|---|
| WO | 2012075112 A1 | 6/2012 |
| WO | 2013022853 A1 | 2/2013 |
| WO | 2013052590 A1 | 4/2013 |

* cited by examiner

ENDOLUMINAL OSTIUM SENSOR ARRAY DEVICE

CROSS-REFERENCE TO RELATED APPLICATIONS

This application claims priority under 35 U.S.C. § 119 to U.S. Provisional Application Ser. No. 61/939,617, filed Feb. 13, 2014, the entirety of which is incorporated herein by reference.

TECHNICAL FIELD

The present disclosure pertains to medical devices. More particularly, the present disclosure relates to devices and systems for sensing endoluminal geometry of blood vessels.

BACKGROUND

Balloon angioplasty and stenting procedures (percutaneous transluminal coronary angioplasty, PTCA) of atherosclerotic lesions in the ostia of arteries branching off from aorta have proven to be difficult. In addition, percutaneous transluminal angioplasty in the ostia of arteries branching off from aorta has been associated with increased risk of operative problems such as ostial trauma, inability to inflate balloon with appropriate guide catheter support, and an increased need for intracoronary manipulation. Similar issues may exist with percutaneous transluminal angioplasty and stenting (PTAS) of renal arteries. Many of the difficulties and risks encountered with conventional techniques used in these procedures can be traced to difficulties in visualizing the geometrical shape of the ostia of arteries.

The geometrical shape of the ostia of arteries cannot be easily visualized using standard visualization techniques such as X-Ray imaging using a C-Arm. The lack of visualization is due to the limitations of 2D X-ray imaging, which is not able to capture the true 3D geometrical shape of the ostia. This impediment of visualization may lead to inaccuracies in balloon angioplasty, deployment of stents, and other complications. For example, if a stent is not positioned correctly and extends beyond the ostium of a vessel, cannulation of another guide wire into the vessel and subsequent access to the vessel becomes extremely difficult. Additionally, if a stent does not appropriately cover the atherosclerotic lesion, the risk of restenosis increases considerably. Thus, accurate placement of a stent at the ostium of an aortic arterial branch is essential.

Recently, devices or methods that assist in placement of stents at ostium of blood vessels have been developed. However, many of these techniques may not provide sufficient information for accurate stent placement and may not be easy to use. Thus, there exists a need in the art to develop medical devices that sense endoluminal ostial geometry of blood vessels to assist in procedures such as PTCA.

SUMMARY

A sensor device may include a shaft having a proximal region and a distal region. A handle may be disposed on the proximal region of the shaft. In addition, an expandable element may be disposed on the distal region of the shaft. The expandable element may be configured to move between a collapsed configuration and an expanded configuration. Additionally, the expandable element may include one or more sensor elements configured to sense proximity of the sensor element to tissue. The handle may include an indicator configured to distinguish between contact of sensor element with tissue, loss of contact and proximity of sensor element to tissue.

A sensor device may have an expandable element configured to be placed on a balloon catheter. The expandable element may be configured to move between a collapsed configuration and an expanded configuration. In addition, the expandable member may include one or more sensor elements configured to sense proximity of the sensor element to the tissue. An indicator may be configured to indicate and distinguish between contact of the sensor element with tissue, loss of contact, and proximity of the sensor element to the tissue.

A method of inserting a stent adjacent a vessel ostium may include providing a catheter with an expandable balloon disposed on a distal end of the catheter, and an expandable stent disposed over the balloon, placing a sensor device over at least a portion of the catheter, the sensor device including at least one flexible arm and at least one sensor element on the flexible arm, the flexible arm moveable between a contracted configuration and an expanded configuration, advancing the catheter through a patient's vasculature to a target site adjacent the ostium, moving the flexible arm to the expanded configuration, measuring proximity and/or contact of the sensor with tissue, and adjusting a position of the catheter to achieve a desired proximity of the sensor to the tissue, and expanding the stent by expanding the balloon.

The above summary of some examples is not intended to describe each disclosed example or every implementation of the present disclosure. The Figures, and Detailed Description, which follow, more particularly exemplify these examples, but are also intended as exemplary and not limiting.

BRIEF DESCRIPTION OF THE DRAWINGS

The disclosure may be more completely understood in consideration of the following detailed description of various examples in connection with the accompanying drawings, in which.

Figure 1:
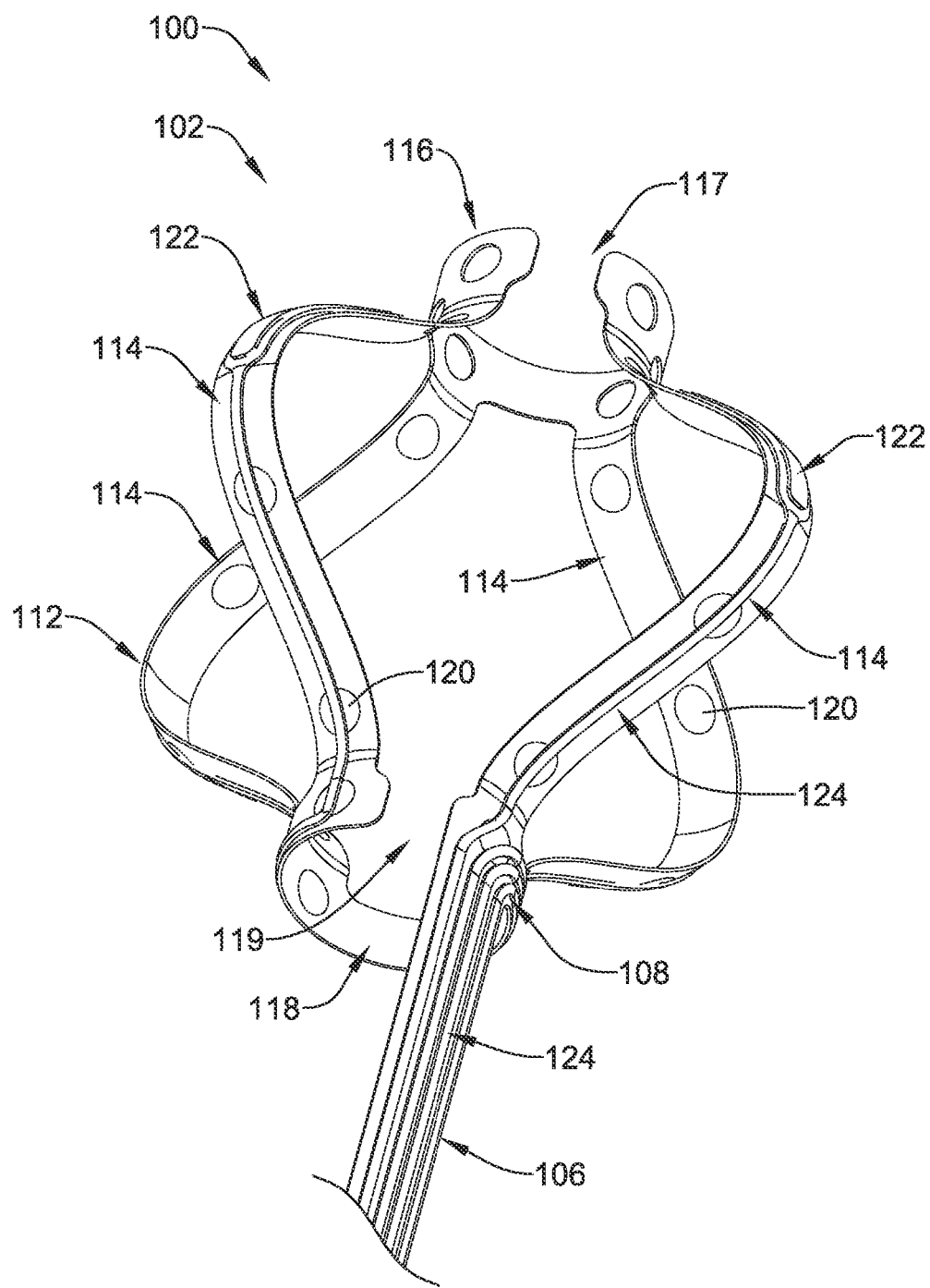
FIG. 1 is a perspective view of a distal section of an exemplary sensor device.

While the disclosure is amenable to various modifications and alternative forms, specifics thereof have been shown by way of example in the drawings and will be described in detail. It should be understood, however, that the intention is not to limit the invention to the particular examples described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate examples of the claimed invention.

Definitions of certain terms are provided below and shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same or substantially the same function or result). In many instances, the terms "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

It is noted that references in the specification to "an example", "some examples", "other examples", etc., indicate that the example(s) described may include a particular feature, structure, or characteristic, but every example may not necessarily include the particular feature, structure, or characteristic. Moreover, such phrases are not necessarily referring to the same example. Further, when a particular feature, structure, or characteristic is described in connection with an example, it would be within the knowledge of one skilled in the art to effect such feature, structure, or characteristic in connection with other examples, whether or not explicitly described, unless clearly stated to the contrary. That is, the various individual elements described below, even if not explicitly shown in a particular combination, are nevertheless contemplated as being combinable or arrangeable with each other to form other additional examples or to complement and/or enrich the described example(s), as would be understood by one of ordinary skill in the art.

The following detailed description should be read with reference to the drawings, in which similar elements in different drawings are identified with the same reference numbers. The drawings, which are not necessarily to scale, depict illustrative examples and are not intended to limit the scope of the disclosure.

Figure 2A:
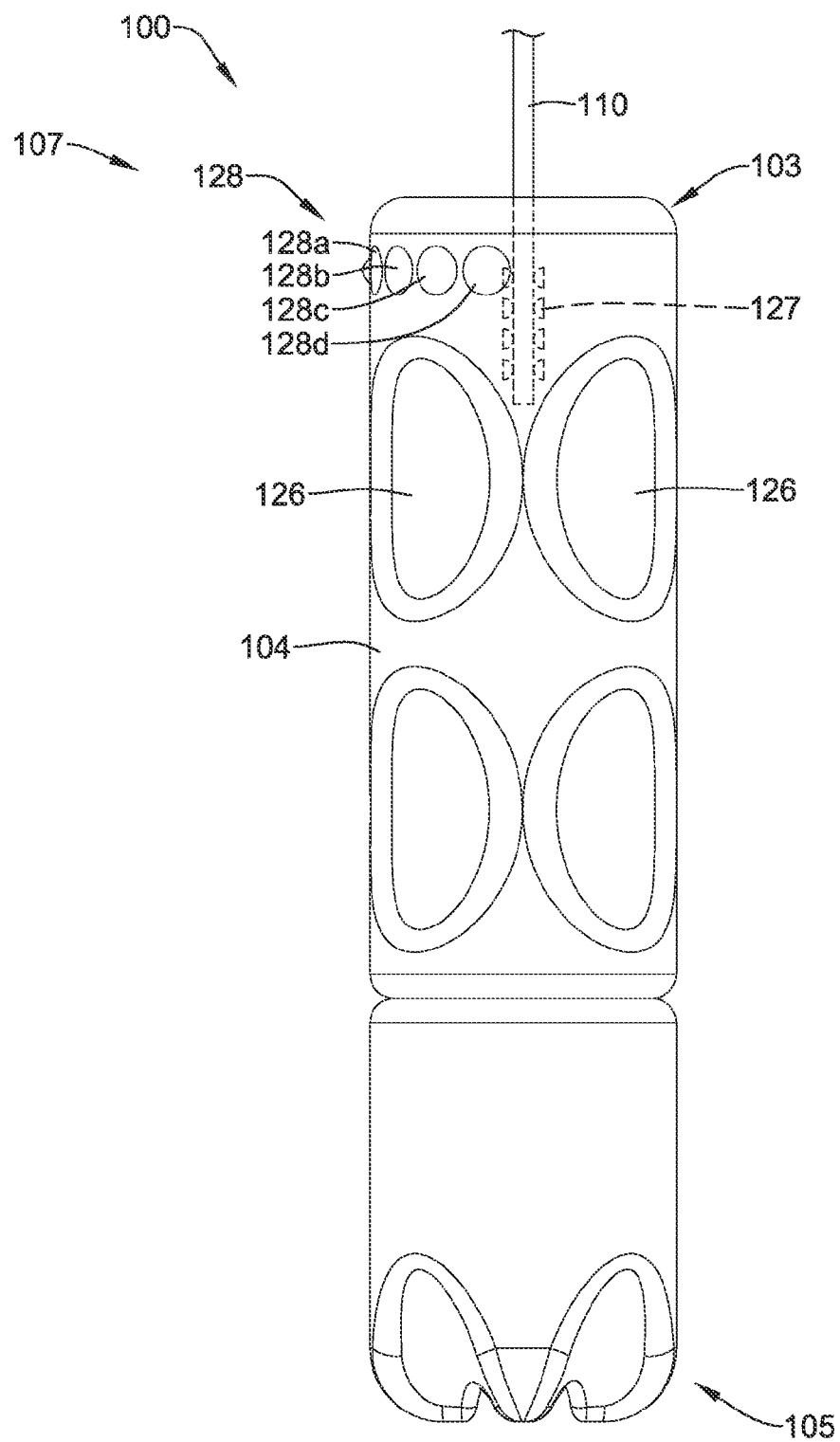
FIG. 2A is a perspective view of a proximal section of an exemplary sensor device.

The present disclosure pertains to medical devices and related methods that can help a user identify an appropriate location for treatment, such as, for example, for placement of a stent, within a vessel ostium. FIG. 1 illustrates a distal section 102 of an exemplary sensor device 100 that can be attached to a balloon catheter to identify an appropriate location for treatment in a blood vessel, by sensing contact with or proximity to tissue. FIG. 1 depicts the distal section 102 of the sensor device 100, and FIG. 2A illustrates a proximal section 107 of the sensor device 100.

As shown in FIG. 1, the distal section 102 may include a shaft 106 having a distal region 108 and a proximal region 110. The distal region 108 of the shaft 106 may connect to an expandable element 112, and the proximal region 110 of the shaft 106 may connect to the proximal section 107 (shown in FIG. 2A).

The shaft 106 may have any suitable shape and dimension. The shaft 106 may be an elongated member having a ribbon, round wire, or tubular shape. In some examples, the shaft 106 may be an elongated hypotube extending between the distal and proximal regions 108, 110. In other examples, as shown, the shaft 106 may be a ribbon shaped cut portion of a cylindrical tube, having a curved shape along its width. The curved shape of the shaft 106 may range between a small arc (as shown) to a full circle, and the shaft 106 may have a curve diameter suitable to dispose over the outer surface of a catheter (not shown). In addition, the shaft 106 may have a length suitable to advance the sensor device 100 to a target location within a patient's vasculature. Further, the shaft 106 may be made of any conducting or non-conducting biocompatible material. Some examples of materials that can be used to make the shaft 106 include metals such as stainless steel, titanium, or the like. In addition, biocompatible polymeric materials such as PEEK, PTFE, or the like, could be used to make the shaft 106.

The expandable element 112, as shown, may include multiple flexible arms 114 joined circumferentially to a distal annular ring 116 and a proximal annular ring 118, forming the expandable element 112. In the illustrated example, the expandable element 112 has a basket shaped configuration or arrangement upon expansion. In other examples, the expandable element 112 may be an expandable spheroid mesh or sheath. Alternatively, the expandable element 112 may form a stent like cylindrical mesh. Other suitable shapes may be contemplated for the expandable element 112.

The expandable element 112 may have an 'n' number of flexible arms 114, where 'n' ranges from two to a feasible number of flexible arms 114 for the dimension of the expandable element 112. In some examples, 'n' may be three, four, five, six or ten. The expandable element 112 may be configured to move back and forth between an expanded configuration, as shown in FIG. 1, and a collapsed configuration. In an expanded configuration, the flexible arms 114 may extend radially outwards, and in a collapsed configuration, the flexible arms 114 may extend substantially straight along the catheter shaft to which the sensor device 100 is attached. The proximal annular ring 118 may connect to the distal region 108 of the shaft 106. In addition, the annular rings 116 and 118 may have slits 117 and 119, respectively, forming a bore configuration to attach to a catheter, described in detail below with FIG. 4. The annular rings 116, 118 may be made of the same material as the flexible arms 114 and/or the shaft 106, or the rings may be made of a different material. The annular rings 116, 118 may be elastic, compressible, and or expandable to fit over a stent delivery system. In some examples, the rings may be made of an elastomeric polymer. Additionally, the distal annular ring 116 may be made of a different material than the proximal annular ring 118.

The expandable element 112 may include one or more holes 120 positioned at one or more locations on the flexible arms 114 and/or the annular rings 116 and 118. The holes 120 may extend partially or completely through the flexible arms 114 and/or the annular rings 116, 118. The holes 120 may be configured to house radiopaque markers or sensors for measurement of physiological parameters, such as blood flow, blood pressure, blood coagulation rate, or the like. In some examples, the radiopaque markers may include a radiopaque element loaded elastomer such as tungsten loaded polyurethane. The holes 120 may have any suitable cross-sectional shape, such as, but not limited to, rectangular, circular, polygonal, or irregular cross-sectional shape. For example, as shown in FIG. 1, the holes 120 may have a circular cross-section. In some examples, the holes 120 may include radiopaque marker material to indicate the position of the sensor device 100 in X-ray imaging. Some examples of radiopaque material that may be used include gold, silver, palladium, platinum, tantalum or the like.

In some examples, the holes 120 may include sensors to measure blood flow and volume to gauge the changes in blood flow before and after a medical procedure. In some other examples, the holes 120 may include sensors to sense the position of a stent. The stent sensors may help a physicians in identifying if the stent has been accurately deployed in the vessel.

Each flexible arm 114 may include one or more sensor elements 122, configured and arranged to distinguish between blood contact and tissue contact. In addition, the sensor elements 122 may be configured to detect proximity to tissue. The sensor elements 122 may be disposed on a distal region of one or more of the flexible arms 114 proximate to the largest circumferential diameter of the expandable element 112. Additionally, one or more sensor elements 122 may be disposed on the annular rings 116 and 118.

In at least some examples, as shown, each sensor element 122 may be configured as an electrode to measure impedance. The electrodes 122 may be operationally connected to a number of conductors 124, such that each electrode 122 is connected to at least one conductor 124. The conductors 124 may be located on the surface of expandable element 112 and the shaft 106, and may connect the electrodes 122 to the proximal section 107 (shown in FIG. 2A).

Referring to FIG. 2A, the proximal section 107 of the sensor device 100 may include a handle 104 to operate the sensor device 100. The handle 104 may have any suitable shape to allow a physician to grip the handle 104. The handle 104 may have a suitable longitudinal length and cross-sectional dimensions that may allow an operator to hold the handle 104 firmly in one hand. For example, as shown, the handle 104 may have a cylindrical shape extending between a distal end 103 and a proximal end 105 having an indentation pattern 126 on the outer surface. In addition, the handle 104 may include a locking mechanism to lock the sensor device 100 to a catheter. One such proximal locking mechanism is described in detail below with reference to FIGS. 2B and 2C.

Figure 2B:
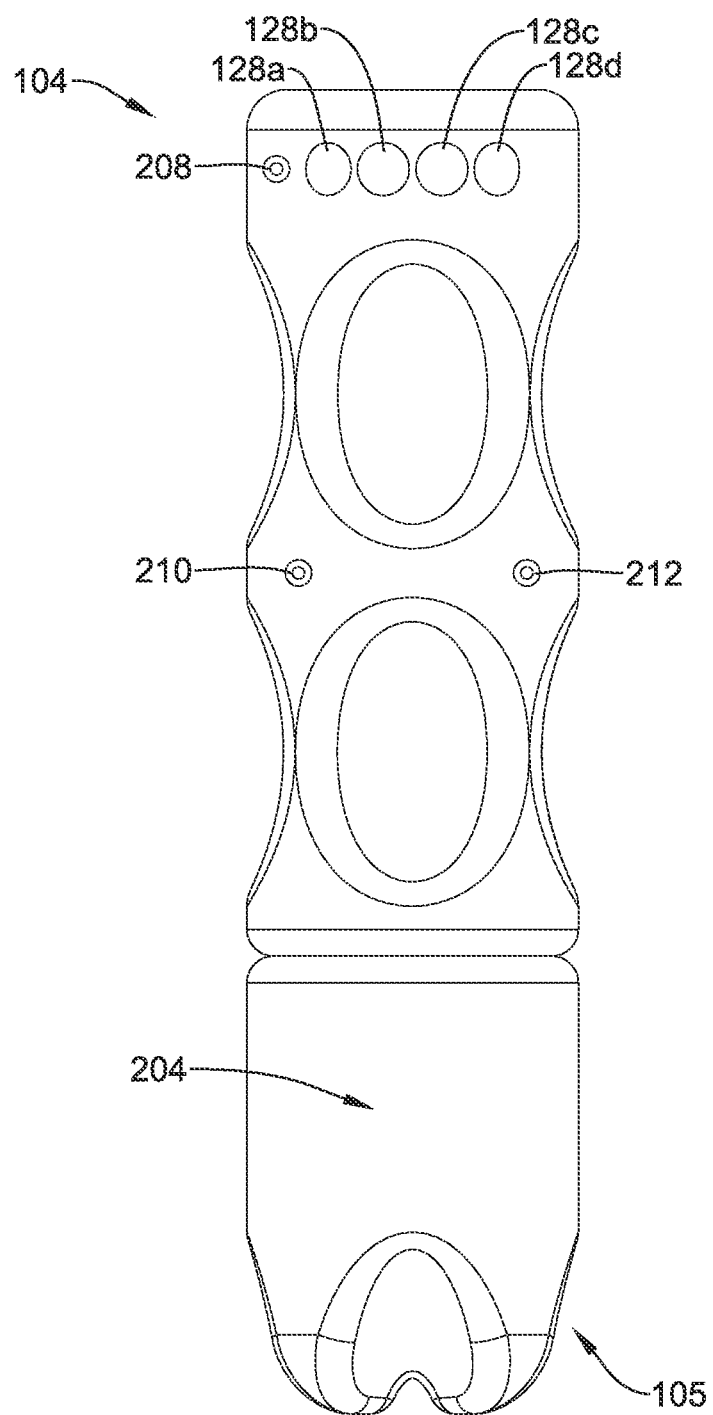
FIG. 2B is a side view of an exemplary handle.

The handle 104 may be detachable from the proximal region 110 of the shaft for ease of use. The handle 104 may house a battery (not shown) and an electronic circuit (not shown). The battery may be rechargeable such that the handle may be reused. The handle 104 may have a battery charging pug in 210. The electronic circuit and the battery may operationally connect the conductors 124 (FIG. 1) to indicators 128. In some examples, one indicator 128 is connected to one conductor 124 and one electrode 122. In the example illustrated in FIGS. 1-2B, four electrodes 122 are disposed on the expandable element 112, one on each flexible arm 114. The electrodes 122 are connected to conductors 124 which are connected to an indicator one or more 128 via an indicator socket contact 127 within the handle 104. The electronic circuit may draw power from the battery, and may be configured to measure impedance at the electrodes 122. In addition, the electronic circuit may be connected to a ground pad (an electrode connected to electrical ground of the electronic circuit) (not shown). The handle 104 may include one or more auxiliary port 212, as shown in FIG. 2B. The auxiliary port 212 may receive a ground pad connector, or may be connected to another monitoring device or a computer. The ground pad may be positioned externally on the body of a patient when the sensor device 100 is used within the patient's vasculature. The ground pad may complete an electrical circuit with the electrodes 122 in the patient's body enabling measurement of tissue impedance between the ground pad and each electrode 122. Alternatively, some electrodes may act as positive electrodes and some as negative electrodes so that a ground pad is not needed. In some examples, the handle 104 may include a stent sensor indicator 208, such as an LED, connected to a stent sensor disposed within a hole 120 on one of the flexible arms 114 or on the distal annular ring 116.

The indicators 128 may be disposed on the outer surface of the handle 104 and may indicate proximity of the electrodes 122 to tissue. The indicator 128 may determine proximity based on the measured impedance at each electrode 122. The indicator 128 may provide distinct visual signals indicating various stages of proximity. The electronic circuit may use the indicator 128 to distinguish between contact of one or more electrode 122 with tissue, loss of tissue contact, and proximity of each electrode 122 to the tissue. In some examples, the indicator 128 may provide an indication of an average distance between a plurality of electrodes 122 and tissue. In other examples, the indicator may only provide an indication of proximity when all electrodes 122 are substantially the same distance from tissue. Such a system may provide information to the user regarding the angle of the expandable element 112 with respect to a vessel ostium.

The electronic circuit may provide these indications to an operator depending upon impedance measurements. The impedance measured between each electrode 122 and the ground pad may vary depending on the location of the electrode 122 within a blood vessel. For example, if the electrode 122 is suspended in blood, the impedance measured at the electrode 122 is significantly lower than the impedance measured when the electrode 122 is in contact with the tissue wall of a blood vessel. In addition, the impedance of each electrode 122 increases as the electrode 122 moves from the center of the blood vessel towards the vessel wall. The increase in measured impedance can be associated with corresponding distance of the electrodes 122 from vessel walls, for example, 5 mm, 4 mm, 3 mm, 2 mm, and 1 mm from the vessel wall.

In some examples, the indicator 128 may include four distinctive visual indicators, such as four lights of different colors, for example, a red light 128*a*, a green light 128*b*, a yellow light 128*c*, and a white light 128*d*. The electronic circuit may switch on each light for a different range of impedance measured at the electrodes 122, thereby indicating a different position of the electrodes 122 within the vasculature of the patient. For example, a red light 128a may indicate contact of an electrode 122 to tissue. A yellow light 128c may indicate tissue not in contact but in close proximity of an electrode 122. For example, a yellow light 128c may indicate the electrode 122 is between 1.0 mm and 2.5 mm away from tissue. A green light 128b may indicate an optimum distance between the electrode 122 and tissue for carrying out a medical procedure, such as deployment of a stent. A white light 128d may indicate that the electrodes 122 are too far from the target tissue, such as, for example, 5 mm or more. The white light 128d may be used to indicate one or both of blood only contact or a distance of 5 mm or more from tissue. In the example shown in FIG. 2A, the indicator 128 includes four separate lights 128a, 128b, 128c, 129d. In other examples, a digital display such as an LED panel may be provided, with a different display indicating the above four stages of proximity. In still other examples, an audio indicator may be included, with a variety of different sounds indicating proximity to tissue contact.

In some examples, the handle 104 may have an array (not shown) of a large number of lights (not shown) dependent on the number of electrodes 122. In the array, a group of four lights may be connected to each electrode 122 to indicate the location of each electrode 122, such that the proximity of each flexible arm 114 may be determined. In some other examples, a multi-color light (not shown) capable of emitting a different color at a different current stimulus may indicate the location of each electrode 122 individually. For example, the multicolor light may emit red, yellow, green, or white light depending upon the location of the corresponding electrode 122.

Alternatively, a display monitor (not shown) may be used as an indicator 128. The impedance signals processed by the electronic circuit may be transmitted through any wired or wireless means to the display monitor. For example, the handle 104 may include a radio transmitter to transmit the impedance measurement to the display monitor. Alternatively the display monitor may be connected directly to the handle 104 via the auxiliary port 212. The display monitor can indicate the impedance measurements from the electrodes 122 in the form of a pattern, a bar graph, chart, or the like.

Figure 2C:
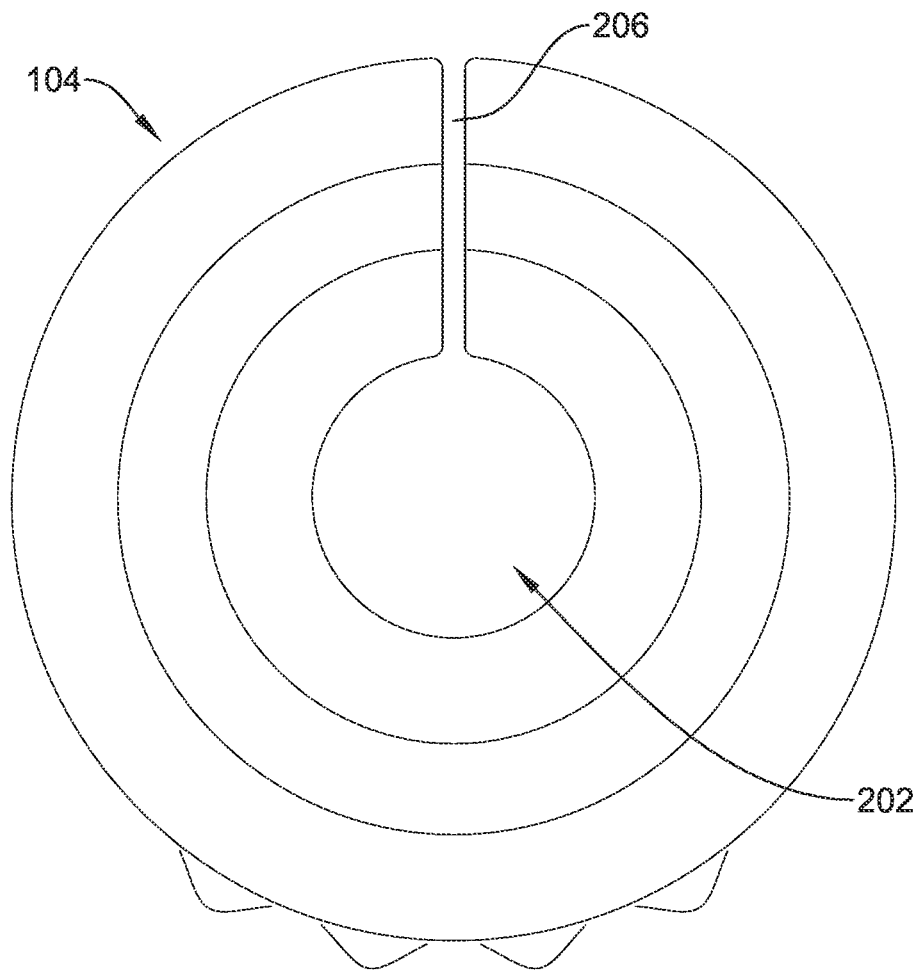
FIG. 2C is a distal end view of the handle of FIG. 2B.
Figure 4:
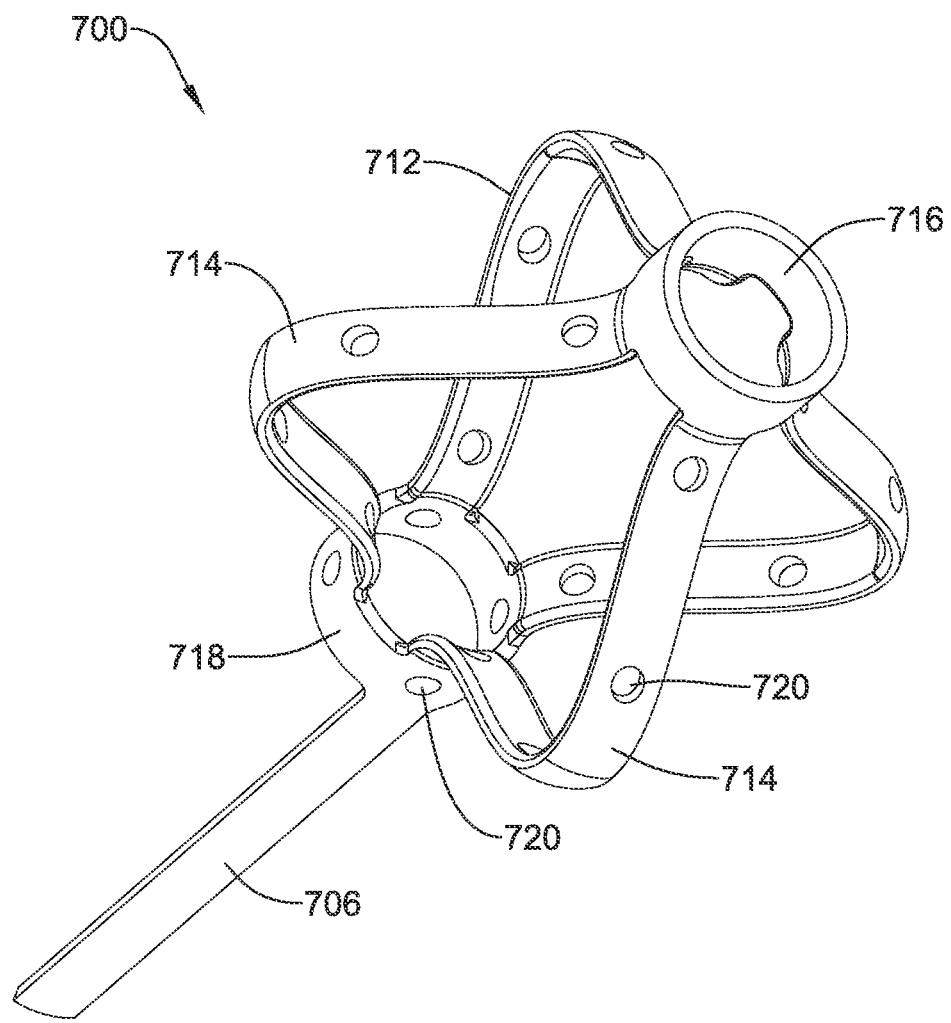
FIG. 4 is a perspective view of an exemplary support structure.

The sensor device 100 may include one or more locking mechanisms to lock the sensor device 100 to a catheter, for example, a balloon catheter. FIGS. 2B, 2C, and 4 illustrate two exemplary locking mechanism, a proximal locking mechanism and a distal locking mechanism. FIGS. 2B and 2C are side view and distal end view, respectively, of the handle 104 of FIG. 2A. A proximal locking mechanism may include an open channel 202 (FIG. 2C) extending longitudinally through the center of the handle 104. The channel 202 may have an adjustable inner diameter. In addition, a twist lock 204 (FIG. 2B) may be attached to the handle 104 at the proximal end 105. In some examples, the twist lock 204 may include a compress grommet. To attach a catheter (not shown) to the sensor device 100, an operator may pass a catheter through slit 206 running longitudinally along the handle 104, and into the channel 202. The balloon catheter may be positioned as desired axially relative to the expandable element 112. For example, the catheter may be advanced until the expandable element 112 resides adjacent the proximal end of the balloon. Upon rotation of the twist lock 204, the channel diameter may be reduced, thereby gripping the catheter firmly to lock it in position. Alternatively, or in addition to the proximal locking mechanism, a distal locking mechanism may be provided. Placing the handle 104 over the proximal end of the balloon catheter may provide an over-the wire configuration.

Figure 3:
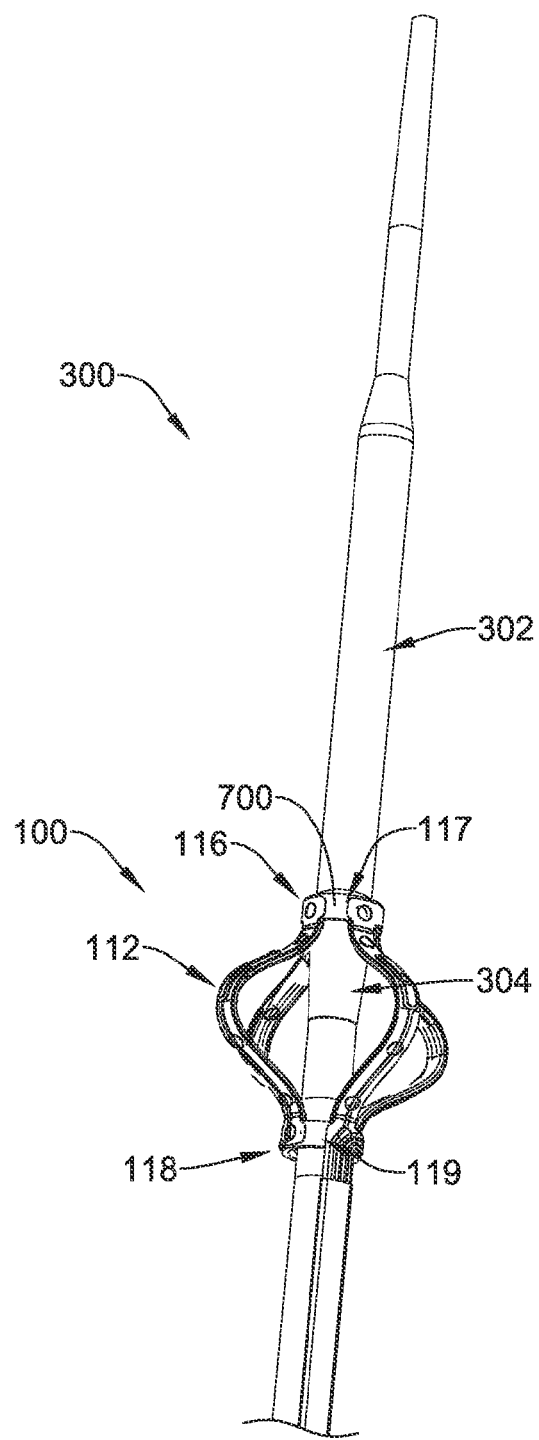
FIG. 3 is a perspective view of a distal part of the sensor device of FIG. 1 disposed on a balloon catheter.

FIG. 3 depicts the distal section 102 of a sensor device 100 attached to a balloon catheter 300 via a distal locking mechanism. Either the proximal or distal ends of the expandable element 112 may be attached or locked onto the catheter 300. In one example, the sensor device 100 may be advanced over the proximal end of the balloon catheter 300, with the proximal end of the catheter being slid through the channel 202 in the handle 104. The sensor device 100 may be advanced over the catheter 300 until the distal annular ring 116 abuts a proximal end of the balloon 302 or another structure on the catheter having a larger diameter than the distal annular ring 116. The distal annular ring 116 may have an inner diameter smaller than the diameter of the folded balloon, thus the annular ring 116 may act as a mechanical stop to prevent the sensor device 100 from moving over the balloon. In examples in which the expandable element 112 is not selfexpandable, the distal annular ring 116 abutting the proximal cone 304 of the balloon 302 may allow the handle 104 to be moved distally thereby moving the flexible arms 114 into the expanded position.

The slits 117 and 119 may be configured to form a bore configuration to receive the balloon catheter 300. The expandable element 112 may be positioned at a location proximate to a proximal end of a balloon 302 of the balloon catheter 300. In some examples, after positioning the expandable element 112 to a desired location on the balloon catheter 300, the annular rings 116 and 118 may be compressed to a smaller diameter by applying external pressure on them. For example, the operator may press the annular rings 116 and 118 with his fingers to reduce their diameter. The reduced diameter of the annular rings 116 and 118 may be less than the outer diameter of the balloon 302. The operator may then push the sensor device 100 forward over the balloon catheter 300, such that the distal annular ring 116 may hit and compress against a proximal cone 304 of the balloon 302. The compressed annular ring 116 on the proximal cone 304 may provide as a light compression mechanical lock. Thus, the compressed annular ring 116 on the proximal cone 304 may lock the sensor device 100 distally to the balloon catheter 300.

In other examples, a stop member (not shown) may be disposed on the catheter 300 and may be configured to engage the proximal annular ring 118. In such an example, a pull-wire (not shown) may be connected to the distal end of the expandable element 112 and to the handle 104. The proximal end 105 of the handle 104 may be pulled proximally to actuate the pull-wire, resulting in expansion of the expandable element 112. In some examples, the twist lock 204 or another section of the handle 104 may be moveable proximally to actuate a pull-wire for expanding the expandable element 112.

In some examples, the sensor device 100 may be disposed over a support member 700. FIG. 4 illustrates an exemplary support member 700 shaped similarly to the expandable element 112, with a shaft 706, and an expandable element 712 defining a plurality of flexible arms 714 and distal and proximal annular rings 716, 718. The annular rings 716, 718 may be circumferentially complete, as shown in FIG. 4, or they may have slits similar to the expandable element 112. In some examples, the support member 700 may have one or more holes 720. The expandable element 112 may be fixedly attached to the support member 700, with the support member 700 providing additional structural stability. The shaft 706 may extend proximally to the handle 104.

Figure 5:
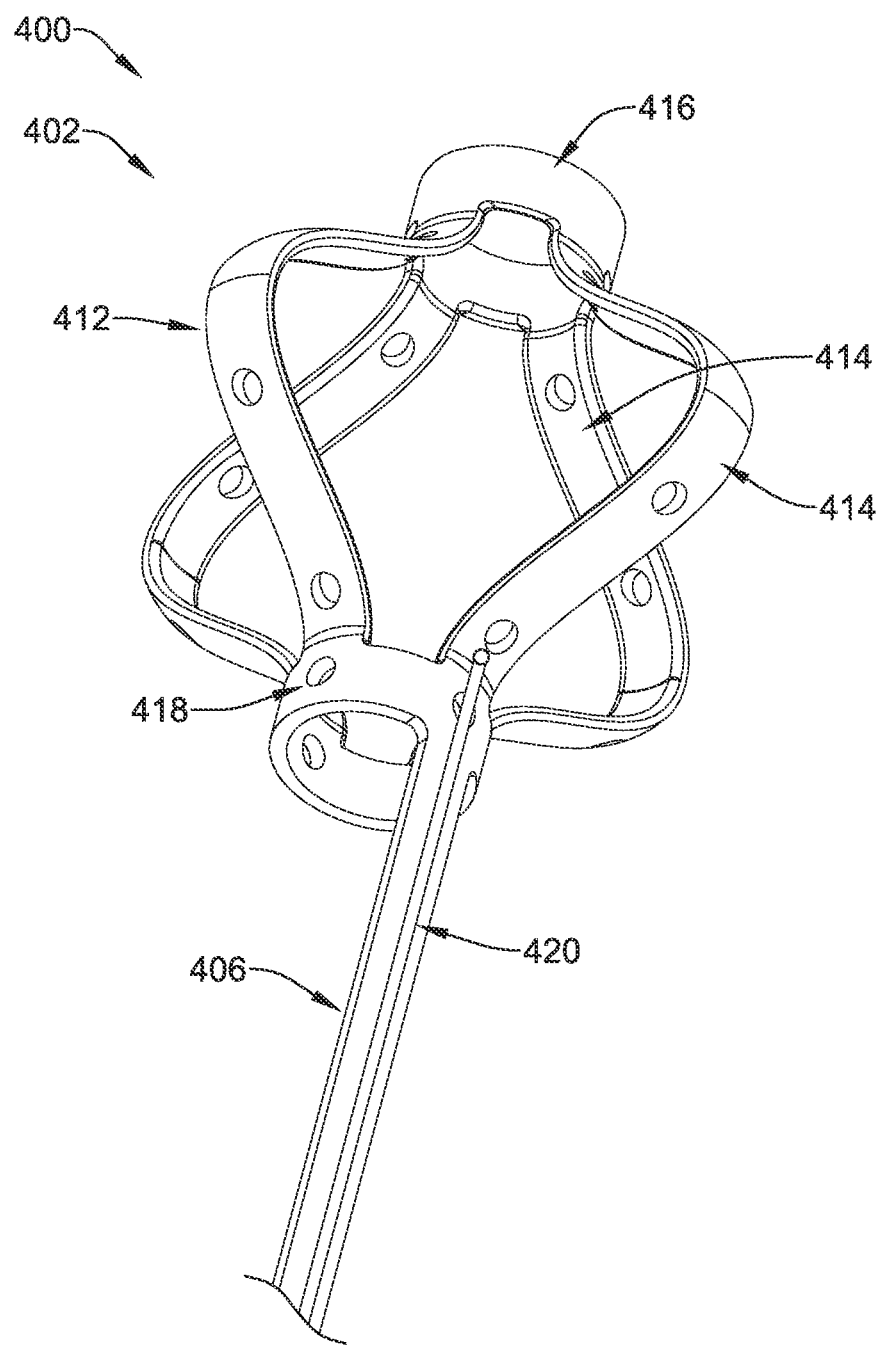
FIG. 5 is a perspective view of a distal part of an alternative exemplary sensor device.

FIG. 5 depicts a distal part 402 of an alternative exemplary sensor device 400 that does not have electrodes 122 on the surface as in the device 100 shown in FIG. 1. Instead, the sensor device 400 may include an expandable element 412 that itself acts as a sensor. The expandable element 412 may have multiple flexible arms 414 and a distal annular ring 416, all made of electrically conducting metallic alloys, such as Nitinol™. In addition, the expandable element 412 may include a proximal annular ring 418 that may be made of insulating biocompatible polymeric materials, such as PEEK, PTFE, PE, or the like. The conducting flexible arms 414 and the distal annular ring 416 together may act a single electrode, and the proximal annular ring 418 may insulate the expandable element 412 from a shaft 406 connected to the proximal end of the expandable element 412. An insulated conductor 420 disposed over the shaft 406, may connect the flexible arms 414 to an electronic circuit in a proximal handle (not shown). The electronic circuit may measure the impedance between the expandable element 412 and a ground pad to identify the location of the distal part in the ostium of a blood vessel.

Figure 6:
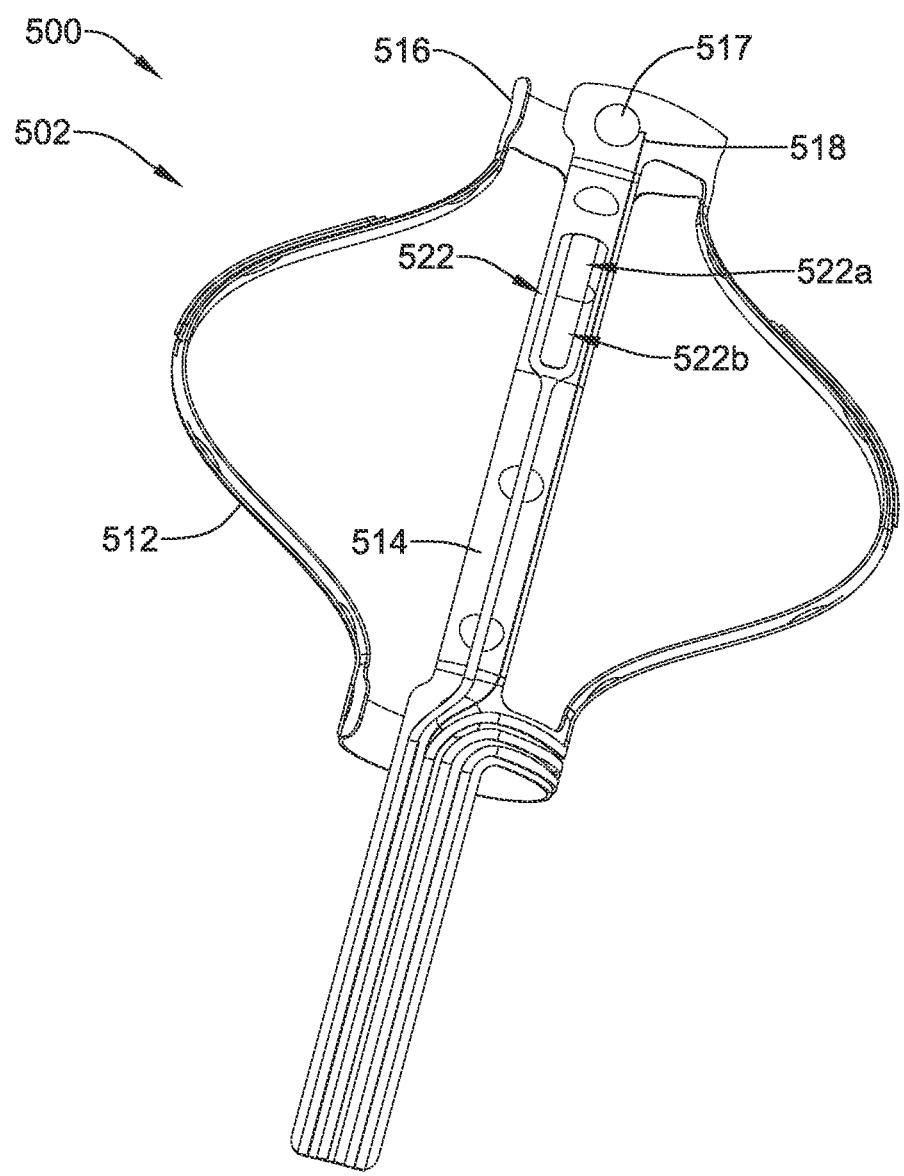
FIG. 6 is a perspective view of a distal part of another exemplary sensor device.

FIG. 6 illustrates a distal part 502 of another exemplary sensor device 500. The sensor device 500 may include an expandable element 512. In addition, the expandable element 512 may include flexible arms 514 having multiple bipolar electrodes 522 to measure tissue impedance. Each bipolar electrode 522 may include a positive electrode 522a and a negative electrode 522b. The use of bipolar electrodes 522 may eliminate the need for a ground pad or electrode, described earlier. The distal ring 516 may include a radiopaque marker. In some examples, a stent sensor 517 may be disposed within the distal ring 516. The stent sensor 517 may have a conductor 518 extending proximally to a stent sensor indicator 208 on the handle 104.

The sensor device disclosed herein may be used in any minimally invasive procedure where imaging modalities cannot reveal sufficient information. For example, one such surgical procedure involves the implantation of a stent in the ostium of an arterial branch of the aorta. The arterial branches of the aorta are eccentric and their ostia are not clearly visible in X-ray imaging methods such as the use of the C-Arm. The sensor device 100 may be used to supplement the imaging methods in accurately guiding a physician in positioning a stent over an atherosclerotic lesion.

Figure 7A:
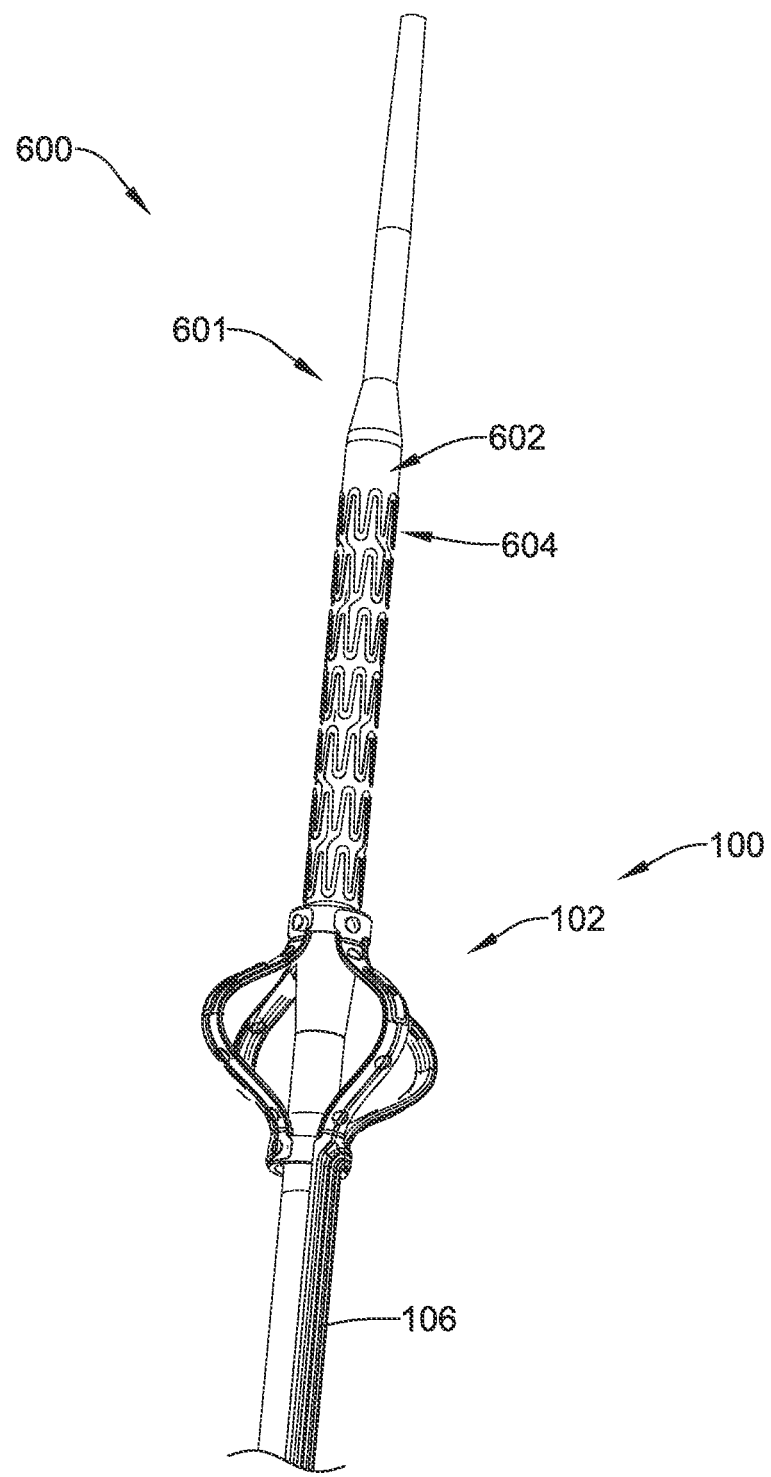
FIG. 7A is a perspective view of the distal portion of an exemplary sensor device disposed on a balloon catheter with a stent.
Figure 7B:
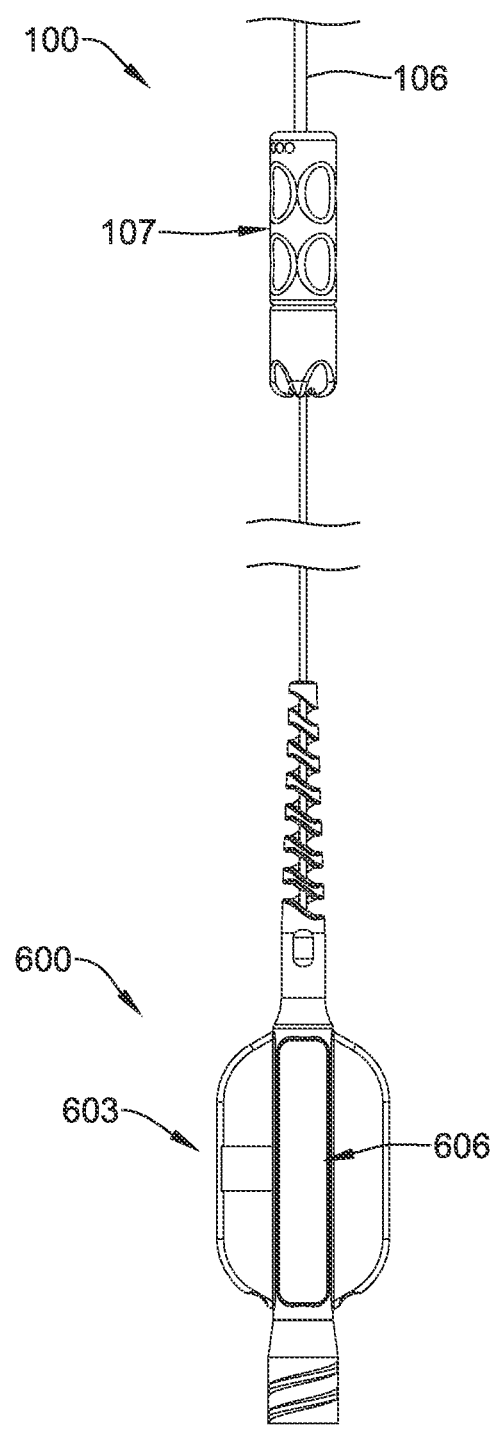
FIG. 7B is a perspective view of the proximal portion of the device of claim 7A.

FIG. 7A illustrates the exemplary sensor device 100 of FIGS. 1-2C disposed over a balloon catheter 600. FIG. 7A depicts the distal section 102 of the sensor device 100 disposed over a distal part 601 of the balloon catheter 600 including a balloon 602 and a balloon expandable stent 604. The sensor device 100 is illustrated in the expanded state. In some examples, the sensor device 100 may be mounted a pre-determined distance from the stent 604, which may allow the sensor device to provide an indication of the location of the stent, possibly reducing or eliminating the need for contrast agent. FIG. 7B depicts the proximal section 107 of the sensor device 100 in an over-the-wire configuration with a proximal part 603 of the balloon catheter 600 having a hub assembly 606 extending from the proximal section 107.

Figure 7C:
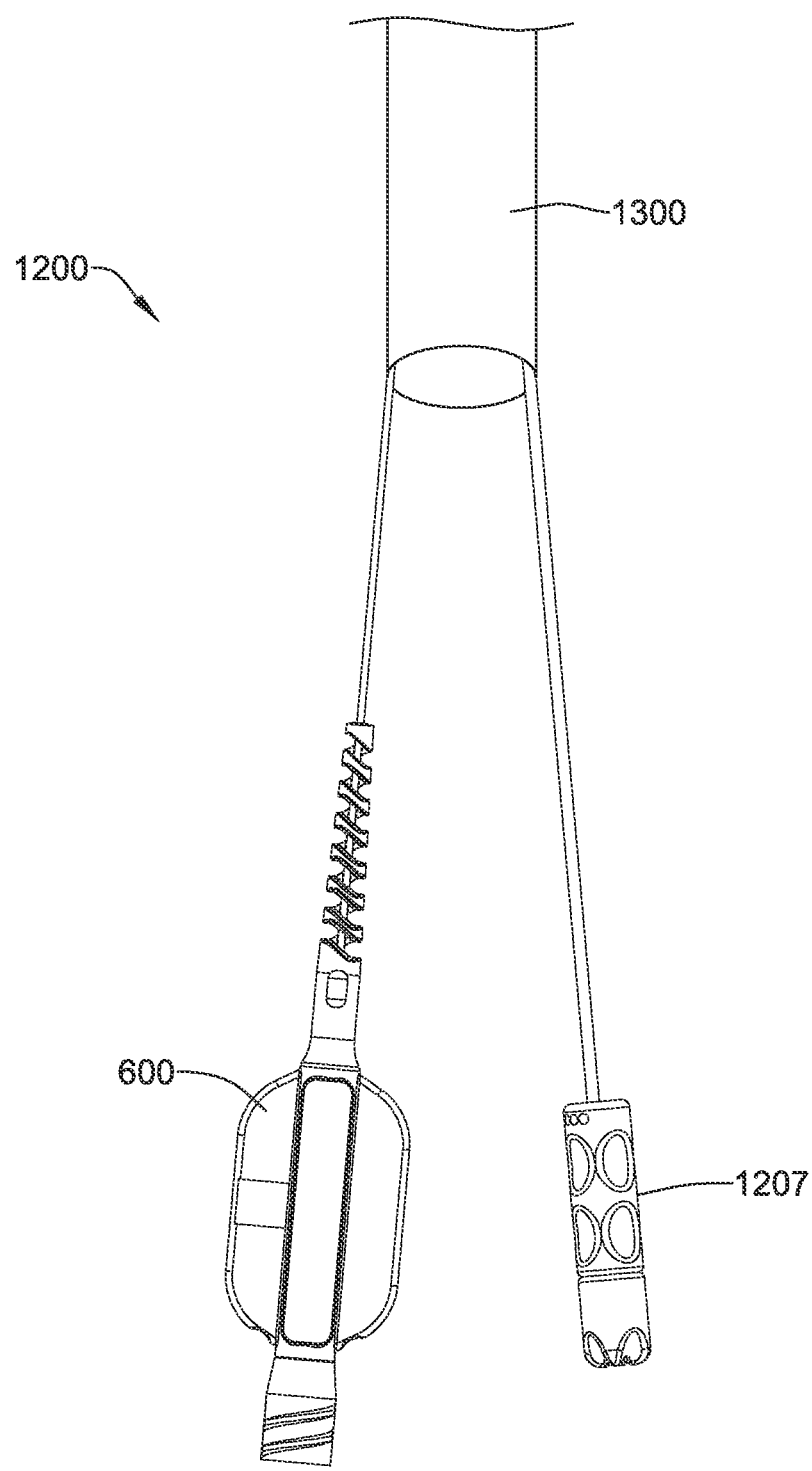
FIG. 7C is a perspective view of the proximal portion of another exemplary sensor device.

FIG. 7C illustrates a rapid exchange configuration in which a sensor device 1200 enters a guide sheath 1300 adjacent the balloon catheter 600. The sensor device 1200 may be similar to the over-the-wire configuration device, with the main difference being the balloon catheter 600 does not extend through a channel 202 in the handle 104. The proximal section 1207 may be similar to the over-the-wire configuration, but may not have the channel 202 and slit 206.

The sensor device 1200 may be positioned over the balloon catheter 600 only at the distal end thereof, with the balloon catheter distal part 601 extending through the expandable element 1200, and the shaft 106 extending adjacent, but not connected, to the balloon catheter.

An operator may cover the balloon with a balloon protector sleeve (not shown), prior to attaching the balloon catheter to the sensor device. The operator may lock the sensor device to the balloon catheter, as discussed previously. The operator may then remove the balloon protector sleeve. Next, the operator may insert a guide wire (not shown) into a patient's vasculature through an incision. The operator may then traverse the guide wire through the patient's vasculature to a target location with the aid of an X-ray imaging modality such as a C-arm. The target location may be an arterial branch of the aorta A such as the coronary artery C having an atherosclerotic lesion at the ostium within the patient's body. The sensor device may be shaped to prevent stent deployment extending into the aorta A when the stent is positioned within the coronary artery C.

Figure 8:
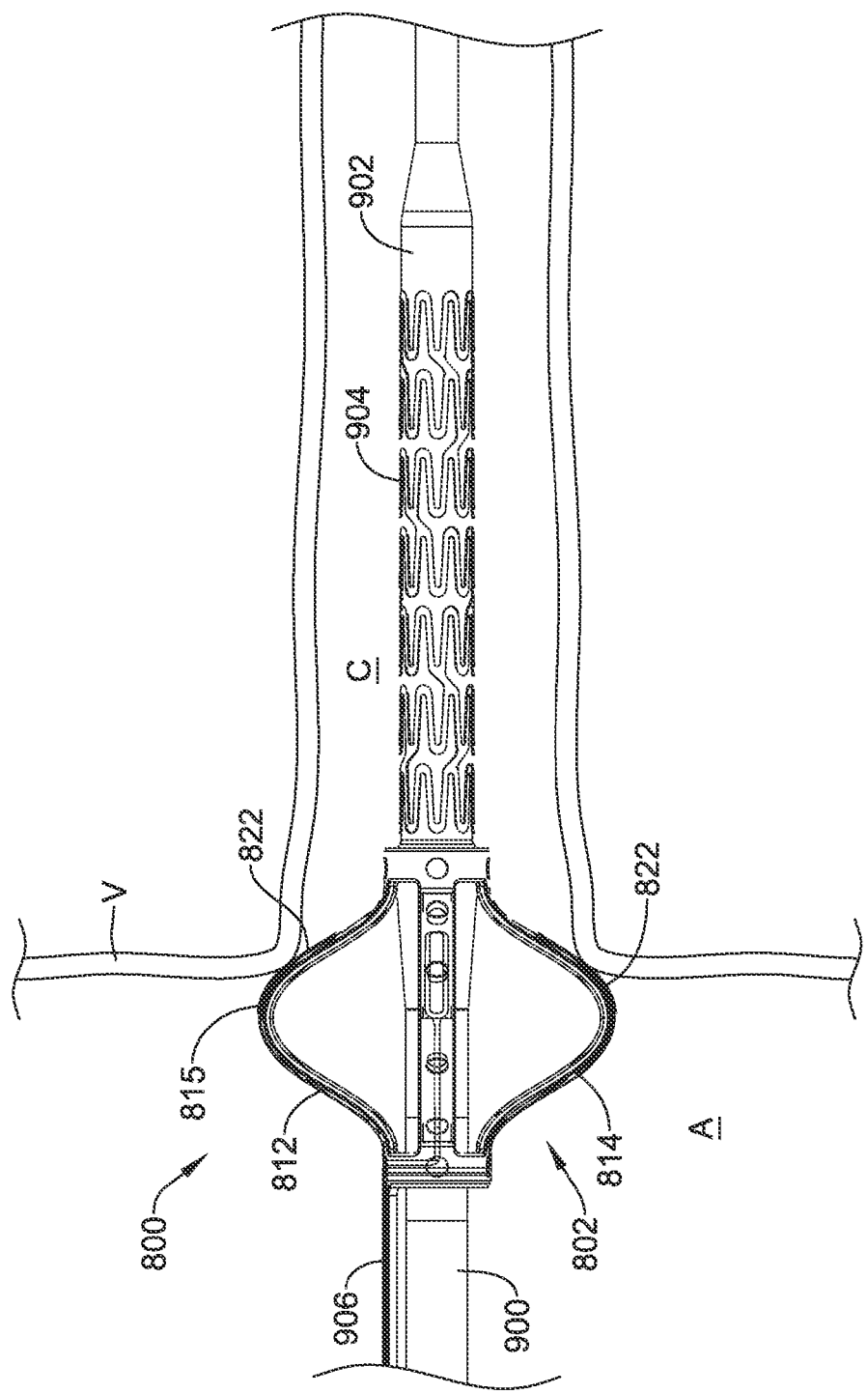
FIG. 8 is a cross-sectional view of a distal part of an alternative exemplary sensor device disposed within the aorta and coronary artery.

The operator may insert a guide catheter (not shown) into the patient's body and traverse it over the guide wire to reach the target location. Then, as shown in FIG. 8, the operator may move the balloon catheter 900 and the sensor device 800 to the target location through the guide catheter with the help of the guide wire. Next, the operator may extend the distal portion of the balloon catheter 900 and the distal section 802 of the sensor device 800 out of the guide catheter and into the ostium. The distal portion of the catheter 900 may include a balloon 902 with a stent 904 thereon, and the sensor device 800 may include expandable element 812.

The expandable element 812 may then be moved to an expanded configuration from a collapsed configuration, as shown in FIG. 8. This may be performed manually by the operator, for example, by moving the shaft 906 in a distal direction. The proximal portion of the sensor device 800 is prevented from moving distally, by being fixedly mounted to the balloon catheter 900 or by abutting a stop or other locking structure. The distally directed force on the shaft 906 may cause the flexible arms 814 to bow outward into the expanded configuration. Alternatively, the flexible arms 814 may be biased in the expanded configuration such that they automatically expand upon moving the sensor device 800 out of the guide catheter. The operator moves the balloon catheter 900 and the sensor device 800 forward and backward adjacent the target site, allowing the operator to determine the optimal location for stent placement based on impedance measurements of the electrodes 822, and the associated lights displayed on the indicator 128. The flexible arms 814 may have peaks 815 which extend radially and provide a geometry of the flexible element 812 that has a larger diameter than the ostium, preventing the expandable element 812 from entering the coronary artery C. The electrodes 822 on the flexible arms 814 may measure impedance which may be used to detect proximity and/or contact with the vessel walls V. In some examples, the sensor device 800 may be mounted a pre-determined distance from the stent 904. Based on the sensed proximity of the sensor device electrodes 822 from the vessel walls V at the ostium and the known distance to the stent, the sensor device may provide accurate deployment of the stent within the coronary artery C, but not extending into the aorta A.

In some examples, the electrodes 822 may be bipolar electrodes which may include a positive electrode and a negative electrode. The use of bipolar electrodes may eliminate the need for a ground pad or electrode, described earlier. The sensor device 800 thus achieves positioning of the stent 904 within the coronary artery C such that upon expansion, the stent does not extend into the aorta A.

Once an optimal location is found, the operator deploys the stent 904 by expanding the balloon 902 at that location. After successful stent deployment, the operator retracts the balloon catheter 900 and the sensor device 800 into the guide catheter and then retracts the guide catheter out of the patient's body.

The materials that can be used for the various components of the sensor device 100, 400, 500, 800, 1200 (and/or other devices disclosed herein) may include those commonly associated with medical devices. For simplicity purposes, the following discussion makes reference to the sensor device 100. However, this is not intended to limit the devices and methods described herein, as the discussion may be applied to other similar tubular members and/or expandable members and/or components of tubular members and/or expandable members disclosed herein.

The sensor device 100 and the various components thereof may be made from a metal, metal alloy, polymer (some examples of which are disclosed below), a metalpolymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some examples the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some examples, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some examples, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some examples, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some examples, the linear elastic and/or non-super-elastic nickel-titanium alloy may be in the range of about 50 to about 60 weight percent nickel, with the remainder being essentially titanium. In some examples, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other examples, a superelastic alloy, for example a superelastic nitinol can be used to achieve desired properties.

In at least some examples, portions of the sensor device 100 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the sensor device 100 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the sensor device 100 to achieve the same result.

In some examples, a degree of Magnetic Resonance Imaging (MRI) compatibility may be imparted into the sensor device 100. For example, portions of device, may be made of a material that does not substantially distort the image and create substantial artifacts (i.e., gaps in the image). Certain ferromagnetic materials, for example, may not be suitable because they may create artifacts in an MRI image. In some of these and in other examples, portions of the sensor device 100 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps, without exceeding the scope of the disclosure. This may include, to the extent that it is appropriate, the use of any of the features of one example in other examples. The disclosure's scope is, of course, defined in the language in which the appended claims are expressed.

What is claimed is:

1. A sensor device, comprising:
a shaft having a proximal region and a distal region;
a handle disposed on the proximal region of the shaft; and
an expandable element disposed on the distal region of the shaft, the expandable element configured to move between a collapsed configuration and an expanded configuration, the expandable element including one or more sensor element configured to sense proximity of the sensor element to tissue, the expandable element having a central axis extending longitudinally therethrough;
wherein the handle includes an indicator configured to distinguish between contact of the sensor element with tissue, loss of contact, and proximity of the sensor element to tissue;
wherein the shaft extends proximally from the expandable element along an axis parallel to but radially spaced away from the central axis;
wherein the expandable element includes proximal and distal annular rings each having a slit that allows a diameter of each annular ring to be reduced by applying external pressure on the ring.

2. The sensor device of claim 1, wherein the expandable element includes two or more flexible arms, each flexible arm is configured to be moveable between the collapsed and expanded configurations, and the two or more flexible arms each include one or more sensor element.

3. The sensor device of claim 2, wherein the expandable element includes a shape memory element defining the two or more flexible arms.

4. The sensor device of claim 2, wherein each flexible arm includes the one or more sensor element disposed on a distal region thereof.

5. The sensor device of claim 1, further comprising a pull wire configured to expand the expandable element.

6. The sensor device of claim 1, wherein the one or more sensor element is configured to distinguish between blood contact and tissue contact.

7. The sensor device of claim 1, wherein the one or more sensor element includes an electrode configured to measure impedance.

8. The sensor device of claim 1, wherein the indicator includes at least four distinct visual indicators.

9. The sensor device of claim 8, wherein the at least four distinct visual indicators include at least four lights with different respective colors.

10. The sensor device of claim 1, wherein the shaft has a ribbon shape with a width measured transverse to the central axis, the width extending only partially circumferentially around the central axis.

11. The sensor device of claim 1, wherein the one or more sensor element is disposed only on a distal region of the expandable element.

12. The sensor device of claim 1, wherein the handle has an open channel extending longitudinally through a center of the handle, the open channel having an adjustable inner diameter.

13. A sensor device, comprising:
an expandable element configured to be placed on a balloon catheter, the expandable element configured to move between a collapsed configuration and an expanded configuration, the expandable element including three or more flexible arms connected to distal and proximal annular rings, each annular ring having a slit that allows a diameter of each annular ring to be reduced by applying external pressure on the annular ring, the flexible arms being spaced apart from one another in both the collapsed configuration and the expanded configuration, each of the three or more flexible arms including an electrically isolated sensor element configured to sense proximity of the sensor element to tissue; and
three or more indicators configured to indicate and distinguish between contact of the sensor elements with tissue, loss of contact, and proximity of the sensor elements to tissue.

14. The sensor device of claim 13, wherein the expandable element is self-expanding and the three or more flexible arms are biased in the expanded configuration.

15. The sensor device of claim 13, wherein the sensor element on each flexible arm includes an electrode configured to measure impedance.

16. The sensor device of claim 13, wherein each of the three or more indicators provides distinct visual signals for each sensor element.

17. The sensor device of claim 13, wherein each sensor element includes a positive and a negative electrode.

18. The sensor device of claim 13, wherein each of the plurality of indicators is connected to a single one of the plurality of sensor elements.

19. The sensor device of claim 13, wherein each of the electrically isolated sensor elements is positioned on a distal region of its flexible arm proximate to a largest circumferential diameter in the expanded configuration.

* * * * *